(12) United States Patent
Hart

(10) Patent No.: US 6,617,428 B1
(45) Date of Patent: Sep. 9, 2003

(54) HUMAN CMRF-35-H9 RECEPTOR WHICH BINDS IGM

(75) Inventor: Derek N. J. Hart, Brisbane (AU)

(73) Assignee: The Corporation of the Trustees of the Order of the Sisters of Mercy in Queensland, South Brisbane (AU)

( * ) Notice: Subject to any disclaimer, the term of this patent is extended or adjusted under 35 U.S.C. 154(b) by 0 days.

(21) Appl. No.: 09/582,934

(22) PCT Filed: Jan. 14, 1999

(86) PCT No.: PCT/NZ99/00003
§ 371 (c)(1),
(2), (4) Date: Jul. 7, 2000

(87) PCT Pub. No.: WO99/36438
PCT Pub. Date: Jul. 22, 1999

(30) Foreign Application Priority Data
Jan. 14, 1998 (NZ) ................................................ 329582

(51) Int. Cl.[7] ...................... C07K 14/705; C12N 15/00; C12N 1/20; C12N 5/02; A61K 38/00

(52) U.S. Cl. .................. 530/350; 435/69.1; 435/320.1; 435/325; 435/252.3; 514/2

(58) Field of Search ................................ 530/350, 395; 514/2; 435/320.1, 325, 69.1, 326, 252.3

(56) References Cited

PUBLICATIONS

Wells, JA Additivity of Mutational Effects in Proteins. Biochemistry 29:8509–8517 (1990).*

Ngo et al. Computational Complexity, Protein Structure Prediction and the Levinthal Paradox. The Protein Folding Problem and Tertiary Structure Prediction. 492–495 Birkhauser Boston (1994).*

Green et al, "The CMRF–35 mAb recognizes a second leukocyte membrane . . . ," International Immunology, vol. 10, No. 7, pp. 891–899 (1998).

Daish et al, "Expression of the CMRF–35 antigen, a new member of the immunoglobulin . . . ," Immunology, vol. 79, pp. 55–63 (1993).

Starling et al, "A novel member of the immunoglobulin gene superfamily recognized . . . ," K. Lever, PCT/NZ99/00003. 1999.

Jackson et al, "Molecular cloning of a novel member of the immunoglobulin . . . ," K. Lever, PCT/NZ99/00003.

* cited by examiner

Primary Examiner—Gary Kunz
Assistant Examiner—Regina M. DeBerry
(74) Attorney, Agent, or Firm—Nixon & Vanderhye

(57) ABSTRACT

Isolated receptor CMRF-35-H9 having an amino acid sequence as set out in SEQ ID NO:1, or a derivative thereof which binds IgM. The receptor, together with peptides encoding its extracellular domain, have application in methods of immunomodulation, including the blocking or inhibition of humoral immune responses in transplant patients.

15 Claims, 10 Drawing Sheets

FIGURE 1

CMRF-35-H9

| 13 | 164 | 24 | 100 |
|----|-----|----|-----|
| A  | B   | C  | D   |

```
cggggggaggcgtgactttccccteggggtccaggtagggcctggagctgctgcaagtgccg 60
                            M  W  L  P  W  A  L  L  L  I  W  V  P  G 14
cctgtgctggggaagggaccATGTGGCTGCCTTGGGCTCTGTTGCTTCTCTGGGTCCCAG 120

C  F  A  L  S  K  C  R  T  V  A  G  P  W  G  S  L  S  V  Q 34
GATGTTTTGCTCTGAGCAAATGCAGGACCGTGGCGGGCCCGTGGGGATCCCTGAGTGTGC 180

C  P  Y  E  K  E  H  R  T  L  N  K  Y  W  C  R  P  P  Q  I 54
AGTGTCCCTATGAGAAGGAACACAGGACCCTCAACAAATACTGGTGCAGACCACCACAGA 240

F  L  C  D  K  I  V  E  T  K  G  S  A  G  K  R  N  G  R  V 74
TTTTCCTATGTGACAAGATTGTGGAGACCAAAGGGTCAGCAGGAAAAAGGAACGGCCGAG 300

S  I  R  D  S  P  A  N  L  S  F  T  V  T  L  E  N  L  T  E 94
TGTCCATCAGGGACAGTCCTGCAAACCTCAGCTTCACAGTGACCCTGGAGAATCTCACAG 360

E  D  A  G  T  Y  W  C  G  V  D  T  P  W  L  R  D  F  H  D 114
AGGAGGATGCAGGCACCTACTGGTGTGGGGTGGATACACCATGGCTCCGAGACTTTCATG 420

P  V  V  E  V  E  V  S  V  F  P  A  S  T  S  M  T  P  A  S 134
ATCCCGTTGTCGAGGTTGAGGTGTCCGTGTTCCCGGCATCAACGTCAATGACACCTGCAA 480

I  T  A  A  K  T  S  T  I  T  T  A  F  P  P  V  S  S  T  T 154
GTATCACTGCGGCCAAGACCTCAACAATCACAACTGCATTTCCACCTGTATCATCCACTA 540

L  F  A  V  G  A  T  H  S  A  S  I  Q  E  E  T  E  E  V  V 174
CCCTGTTTGCAGTGGGTGCCACCCACAGTGCCAGCATCCAGGAGGAAACTGAGGAGGTGG 600

N  S  Q  L  P  L  L  L  S  L  L  A  L  L  L  L  L  V  G 194
TGAACTCACAGCTCCCGCTGCTCCTCTCCCTGCTGGCATTGTTGCTGCTTCTGTTGGTGG 660

A  S  L  L  A  W  R  M  F  Q  K  W  I  K  W  I  K  A  G  D 214
GGGCCTCCCTGCTAGCCTGGAGGATGTTTCAGAAATGGATCAAATGGATCAAAGCTGGTG 720

H  S  E  L  S  Q  N  P  K  Q  A  A  T  Q  S  E  L  H  Y  A 234
ACCATTCAGAGCTGTCCCAGAACCCCAAGCAGGCTGCCACGCAGAGTGAGCTGCACTACG 780

N  L  E  L  L  M  W  P  L  Q  E  K  P  A  P  P  R  E  V  E 254
CAAATCTGGAGCTGCTGATGTGGCCTCTGCAGGAAAAGCCAGCACCACCAAGGGAGGTGG 840

V  E  Y  S  T  V  A  S  P  R  E  E  L  H  Y  A  S  V  V  F 274
AGGTGGAATACAGCACTGTGGCCTCCCCCAGGGAAGAACTTCACTATGCCTCGGTGGTGT 900

D  S  N  T  N  R  I  A  A  Q  R  P  R  E  E  E  P  D  S  D 294
TTGATTCTAACACCAACAGGATAGCTGCTCAGAGGCCTCGGGAGGAGGAACCAGATTCAG 960
```

FIGURE 2A

```
        Y  S  V  I  R  K  T  *                                301
ATTACAGTGTGATAAGGAAGACATaggtcctgcctcgccatcggagctctcatgggcccc  1020
aggaagtcagggacagctcccttatacctggcccacgtccttctcagcctgccctcgaca  1080
acagtgaccaacagacaggcagctgggtttccaggccatccctctgttgccatcagcttg  1140
attggcttccccgagggccagcagggctggggctccggagagcagcaggaagcactccca  1200
gccaccagtgcctgtcacctctttccctttgccctgcttcatcccagctctgtgtgtg    1260
gaggacaaagcttcttcctgcgtggctccaggaaaagatgtggctcacgtaggtNgcacc  1320
tgccaatagctttgtcaatcacagccccataggaacgtctggaattgcttgggagttggg  1380
gagaactgtcaagaagagtgaagagagtgccaaagcggagatctgttcacctgggtggag  1440
gggaccactaagatcaagatcaaagattctccccatctcacagacaaggaaactgagNNa  1500
gagggaggagagaattgctcatggctccagaactggtggcaagtttctctggactcttta  1560
ggtttattttaatatgaaatataaaaacagtttcaaatatcttattgagggagaagtaa   1620
aaacttatttaaaccccg                                            1640
```

FIGURE 2B

EXPRESSION OF CMRF-35 BY LCELL TRANSFECTANTS
L Cells
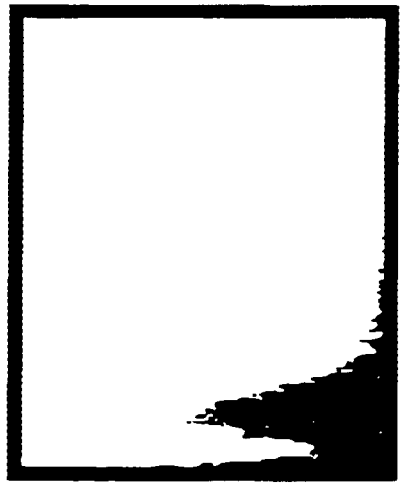
CMRF-35 Transfectants
PANEL A
PANEL B
FLUORESENCE INTENSITY
FIGURE 3

Reactivity of mAb with CMRF-35-Ig Fusion Protein

|  |  | CMRF-35-Ig | CD33-Ig |
|---|---|---|---|
| IgG2a | CMRF-35- mAb |  |  |
| IgG2a | Sal 5 |  |  |
| IgG1 | 1B5,G9 |  |  |
| IgM | 2E9,A10 |  |  |

HUMAN CMRF-35-H9 RECEPTOR WHICH BINDS IGM

This application is a 371 application of PCT/NZ99/00003, filed Jan. 14, 1999, and claims priority from New Zealand Prior 329582 filed Jan. 14,1998.

FIELD OF THE INVENTION

This invention relates to the receptor CMRF-35-H9 which inter alia binds immunoglobulin M(IgM)

BACKGROUND OF THE INVENTION

It is well known that the human immune response is stimulated by foreign antigen (Ag). Antigen presenting cells, such as the dendritic cells perform important immunoregulatory functions by presenting antigens in the form of peptides bound to cell-surface major histocompatibility complex (MHC) molecules to T cells. This initiates a T lymphocyte response which is followed by a humoral or antibody (B lymphocyte derived) immune response. Humoral responses include a primary response with antibodies of the IgM isotype followed by a secondary response with immunoglobulin of the IgG, IgA and IgE isotype. The soluble immunoglobulin interact with Ag in the tissues (opsonisation) and bind, via their functional components (Fc) to receptors (Fc receptors) on different types of white blood cells.

Given that IgM is the primary antibody produced, the identification and characterisation of cellular IgM receptors and binding proteins has important implications in manipulating immune response in prophylaxis and therapy, particularly in humans.

The applicant has now identified a receptor on human dendritic and other cells which binds IgM. It is broadly to this receptor, which the applicants have called CMRF-35-H9, that the present invention is directed.

SUMMARY OF THE INVENTION

The present invention has a number of aspects. In a first aspect, the invention provides human CMRF-35-H9 which has the amino acid sequence set out in FIG. 2 (SEQ ID NO. 1), or a functionally equivalent variant thereof.

In a further aspect, the invention provides a peptide encoding domain of receptor CMRF-35-H9, which is comprised of amino acids 14 to 177 of the amino acid sequence of FIG. 2 (SEQ ID NO. 3), or a functionally equivalent variant thereof.

In a still further aspect, the invention provides a polynucleotide encoding receptor CMRF-35-H9 and/or its extracellular domain as defined above. This polynucleotide molecule is preferably DNA, more preferably cDNA, but can also be RNA.

In one embodiment, the DNA molecule coding for receptor CMRF-35-H9 comprises the nucleotide sequence set out in FIG. 2 (SEQ ID NO. 4), or a sequence which is a functionally equivalent variant thereof.

In a further embodiment, the present invention provides a DNA molecule coding for a peptide encoding the extracellular domain of human CMRF-35-H9 which comprises nucleotides 120 to 611 of FIG. 2 (SEQ ID NO. 6).

In yet a further aspect, the invention provides a vector including a polynucleotide as defined above.

In still a further aspect, the invention provides a method of producing receptor CMRF-35-H9 or the extracellular domain thereof comprising the steps of:

(a) culturing a suitable host cell which has been transformed or transfected with a vector as defined above to express the encoded receptor CMRF-35-H9 or extracellular domain; and (b) recovering the expressed receptor CMRF-35H9 or extracellular domain.

In a still further aspect, the present invention provides for the use of receptor CMRF-35-H9 or extracellular domain thereof in the preparation of a medicament suitable for use in methods of therapy or prophylaxis.

Pharmaceutical compositions comprising receptor CMRF-35-H9 or the extracellular domain thereof also form part of the present invention.

Other aspects of the invention will be apparent from the description which follows and from the attached claims.

DESCRIPTION OF THE DRAWINGS

While the invention is broadly as defined above, it will be appreciated by those persons skilled in this art that it is not limited thereto and that it includes embodiments more particularly described below.

In particular, preferred aspects of the invention will be described in relation to the accompanying drawings in which:

FIG. 1 represents the structure of the receptor of the invention wherein:

A is a 13 amino acid hydrophobic leader sequence;
B is a 164 amino acid extracellular domain;
C is a 24 amino acid transmembrane region; and
D is a 100 amino acid cytoplasmic domain.

FIG. 2 represents both the amino acid sequence (SEQ ID NOs:1, 2 and 3) of the CMRF-35-H9 receptor of the invention and the nucleotides coding therefor (SEQ ID NOs:4, 5 and 6). SEQ ID NO:1 and SEQ ID NO:4 represent the full length wild type amino acid and nucleic acid sequences of CMRF-35-H9, respectively. SEQ ID NO:3 and SEQ ID NO:6 represent the wild type amino acid and nucleic acid sequence of the extra cellular domain of CMRF-35-H9, respectively. SEQ ID NO:2 and SEQ ID NO:5 represent amino acid and nucleic acid sequence variants of CMRF-35-H9, respectively. The leader sequence and transmembrane region are underlined. The putative IgM binding domain within the extracellular domain is shown in square brackets. "N" in the sequence indicates an undetermined nucleotide.

FIG. 3 depicts L cells transfected with the CMRF-35 cDNA binding the CMRF-35 mAb. Panel A shows reactivity of the CMRF-35 mAb with the parental L cells. Panel B is the histogram for the CMRF-35 mAb reactivity with the L-cell transfectants expressing CMRF-35 cDNA.

Figure 4:
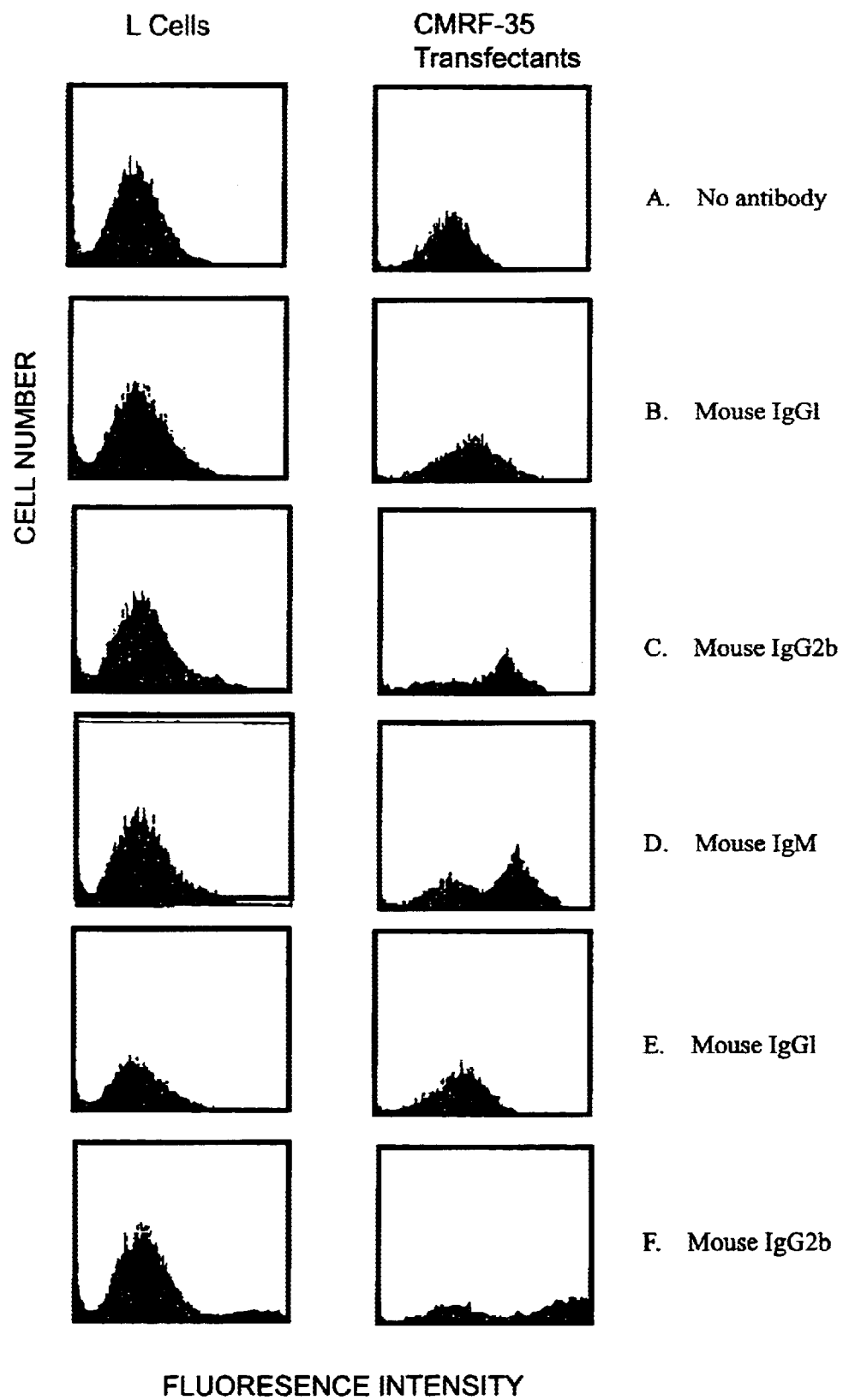

FIG. 4 depicts binding of mouse immunoglobulin to the L cell transfectants. The histograms on the left of the diagram shows the reactivity of mouse immunoglobulins to L cells. On the right are the histograms for the reactivity of mouse immunoglobulins to the CMRF-35 expressing transfectants. A—no primary antibody, B—IgG1, C—IgG2b, D—IgM, E—IgG1 and F—IgG2b.

Figure 5:
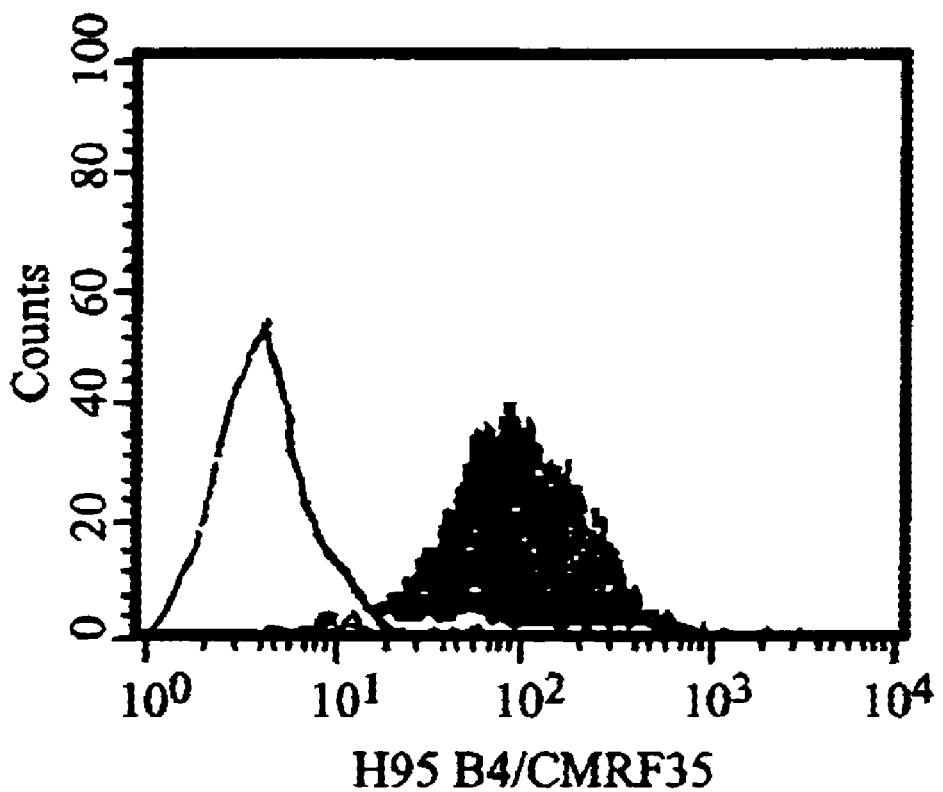

FIG. 5 depicts Jurkat cells transfected either with CMRF-35-H9 cDNAs expressing epitopes reacting with the CMRF-35 mAb. A single line indicates Jurkat cells transfected with vector alone.

Figure 6A:
Figure 6B:

FIG. 6 depicted are transfected lines resetting with human RBC coated with mouse antibodies of the IgM isotype (FIG. 6a) but not IgG2b isotypes (FIG. 6b).

Figure 7:
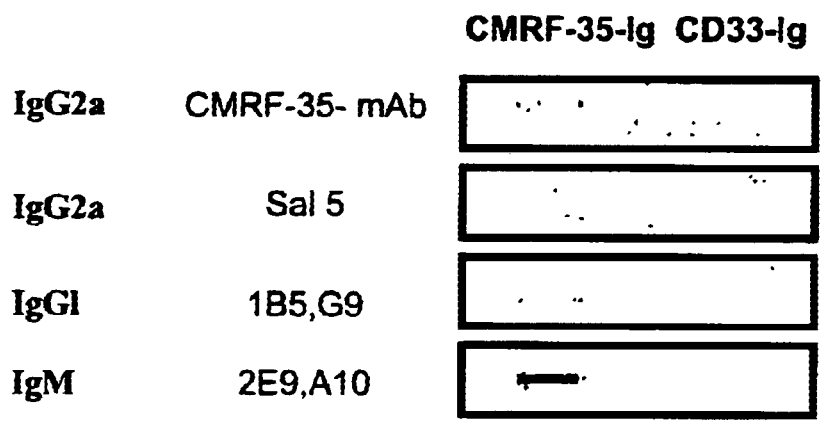

FIG. 7 the CMRF-35-Ig fusion protein is depicted binding mouse IgM but not mouse IgG2a or IgG 1.

Figure 8:
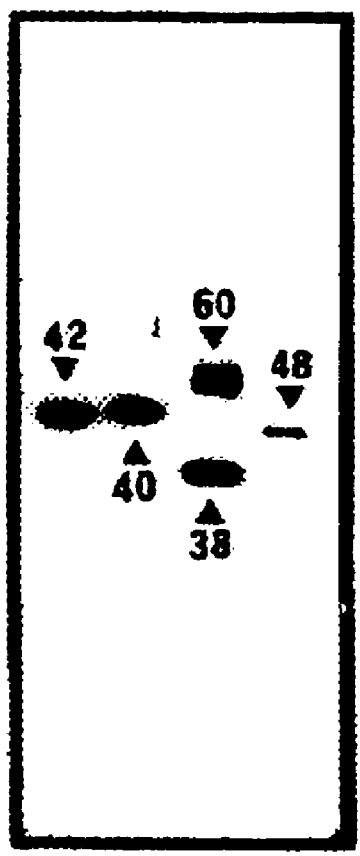

FIG. 8 is an autoradiograph of cell lines transfected with CMRF-35-H9, CMRF-35 and vector only, as well as untransfected cell lines, when reacted with IgM isotype mAb CMRF-75.

DESCRIPTION OF THE INVENTION

A. Human CMRF-35-H9

Human CMRF-35-H9 of the invention is a new member of the immunoglobulin (Ig) gene superfamily. More importantly, CMRF-35-H9 binds IgM. The general structure for the receptor is given in FIG. 1. The receptor has the amino acid and nucleotide sequences shown in FIG. 2.

Individual amino acids are represented by the single letter code as follows:

| Amino Acid | Three-letter abbreviation | One-letter symbol |
| --- | --- | --- |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic Acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The amino acid sequence includes a 13 amino acid leader sequence, a 164 ammo acid extracellular domain, a 24 amino acid transmembrane region and a 100 amino acid cytoplasmic region.

The extracellular domain further includes an Ig binding domain approximately from amino acids 29 to 126 of FIG. 2. This domain includes two sites for N-linked glycosylation between amino acids 82 to 84 and 91 to 93.

The membrane proximal region of 45 amino acids contains a number of serine and threonine residues suggesting that this region may contain some O-linked glycosylation. In addition, the region contains proline residues indicating that this hinge region may form a fairly rigid structure.

The 100 amino acid cytoplasmic region of human CMRF-35-H9 contains four tyrosine-containing motifs. By analogy with similar motifs in other transmembrane regions this suggests that this molecule may have a signal transduction role, either positively or negatively.

Human CMRF-35-H9 can usefully be provided in a number of different forms. These include human CMRF-35-H9 itself, the "mature" form of human CMRF-35-H9, and the extracellular receptor domain of human CMRF-35-H9.

The "mature" form of human CMRF-35-H9 of the invention is human CMRF-35-H9 less its native amino-terminus leader or signal sequence, whereas the extracellular receptor domain is human CMRF-35-H9 lacking both the transmembrane region and cytoplasmic domain (where present).

The invention is of course not restricted to receptors having the specific sequences of FIG. 2. Functionally equivalent variants are also contemplated.

The phrase "functionally equivalent variants" recognises that it is possible to vary the amino acid sequence of a protein while retaining substantially equivalent functionality. For example, a protein can be considered a functional equivalent of another protein for a specific function if the equivalent protein is immunologically cross-reactive with and has at least substantially the same function as the original protein. The equivalent can be, for example, a fragment of the protein, a smaller-sized version of the protein from which one or more amino acids (such as amino acids 210 to 212 of the FIG. 2 sequence) have been deleted (resulting in SEQ ID NO. 2), a fusion of the protein with another protein or carrier, or a fusion of the protein or of a fragment with additional amino acids. It is also possible to substitute amino acids in a sequence with equivalent amino acids using conventional techniques. Groups of amino acids normally held to be equivalent are:

(a) Ala, Ser, Thr, Pro, Gly;
(b) Asn, Asp, Glu, Gln;
(c) His, Arg, Lys;
(d) Met, Leu, Ile, Val; and
(e) Phe, Tyr, Trp.

Homologs to human CMRF-35-H9 in other mammals are also "functionally equivalent variants" in the sense this phrase is used herein.

The probability of one amino acid sequence being functionally equivalent to another can be measured by the computer algorithms BLASTP (Altschul et al 1990 *J Mol Biol* 215:403–410).

Collectively, all of the above constitute "receptor CMRF-35-H9".

Receptor CMRF-35-H9 of the invention or its extracellular receptor domains may be prepared by methods known in the art. Such methods include protein synthesis from individual amino acids as described by Stuart and Young in "Solid Phase Peptide Synthesis", Second Edition, Pierce Chemical Company (1984). It is however preferred that human CMRF-35-H9 and/or its extracellular receptor domain be prepared by recombinant methods.

B. Polynucleotides Encoding Receptor CMRF-35-H9

In another aspect of this invention, the applicants provide polynucleotides encoding receptor CMRF-35-H9 or its extracellular domain. These polynucleotides may be DNA (isolated from nature, synthesised or cDNA) or RNA. Most often, the polynucleotides will be cDNA.

In one embodiment, the polynucleotide of the invention comprises the nucleotides encoded by the sequence of FIG. 2, or the coding region thereof between substantially nucleotides 81 to 986. In a further embodiment the polynucleotide comprises the molecule encoded by nucleotides 120 to 611.

Again, the invention is not restricted to polynucleotides having the specific sequence of FIG. 2. Functionally equivalent variants of the FIG. 2 sequence are also contemplated, including the polynucleotide having the sequence of SEQ ID NO. 5.

The phrase "functionally equivalent variants" recognises that it is possible to vary the nucleotide sequence coding for a protein and to still express either the same protein (having the same amino acid sequence due to the degeneracy of the nucleic acid code) or a protein having equivalent functionality.

The probability of one nucleic acid nucleotide being functionally equivalent to another can be measured by the computer algorithm, including by FASTA (Pearson et al 1988 *Proc. Natl. Acad Sci.* 85 2444–2448).

Nucleotide sequences coding for homologs to human CMRF-35-H9 in other mammals are also contemplated as "functionally equivalent variants" as this term is used herein.

C. Recombinant Expression of Human CMRF-35-H9

In yet another aspect, the present invention relates to the recombinant expression of receptor CMRF-35-H9 or its extracellular domain.

The polynucleotides that encode CMRF-35-H9 or the extracellular domain may be inserted into known vectors for use in standard recombinant DNA expression protocols. Standard recombinant techniques are those such as are described in Sambrook et al.; "Molecular Cloning" 2nd Edition Cold Spring Harbour Laboratory Press (1987) and by Ausubel et al., Eds, "Current Protocols in Molecular Biology" Greene Publishing Associates and Wiley-Interscience, New York (1987).

Vectors useful in eucaryotes such as yeast are available and well known. A suitable example is the 2 m plasmid.

Suitable vectors for use in mammalian cells are also known. Such vectors include pcDNA3 (Invitrogen) well-known derivatives of SV-40, adenovirus, retrovirus-derived DNA sequences and vectors derived from combination of plasmids and phage DNA.

A presently preferred mammalian cell expression vector is pcDNA3 Invitrogen).

Further eucaryotic expression vectors are known in the art (e.g. P. J. Southern and P. Berg, *J. Mol. Appl. Genet.* 1: 327–341 (1982); S. Subramani et al., *Mol. Cell. Biol.* 1: 854–864 (1981); R. J. Kaufmann and P. A. Sharp, "Amplification And Expression of Sequences Cotransfected with a Modular Dihydrofolate Reductase Complementary DNA Gene," *J. Mol. Biol.* 159: 601–621 (1982); R. J. Kaufmann and P. A. Sharp, *Mol. Cell. Biol.* 159: 601–664 (1982); S. I. Scahill et al, "Expression And Characterization Of The Product Of A Human Immune Interferon DNA Gene In Chinese Hamster Ovary Cells," *Proc. Natl. Acad. Sci. USA* 80: 4654–4659 (1983); G. Urlaub and L. A. Chasin, *Proc. Natl. Acad. Sci. USA* 77: 4216–4220, (1980); D. Simmons "Cloning cell surface molecules by transient expression in mammalian cells" in *Cellular Interactions in Development—A Practical Approach;* Ed. D. Hartley, Oxford University Press (1993).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g. the promoter for 3-phosphoglycerate kinase, the promoters of yeast acid phosphatase, e.g. Pho5, the promoters of the yeast alpha-mating factors, and promoters derived from cytomegalovirus (CMV), polyoma, adenovirus, retrovirus, and simian virus, e.g. the early and late promoters or SV40, and other sequences known to control the expression of genes of eucaryotic cells and their viruses or combinations thereof.

A presently preferred promoter is a CMV promoter.

In the construction of a vector it is also an advantage to be able to distinguish the vector incorporating the foreign DNA from unmodified vectors by a convenient and rapid assay. Such assays include measurable colour changes, antibiotic resistance and the like. In one preferred vector, the β-galactosidase gene is used, which gene is detectable by clones exhibiting a blue phenotype on X-gel plates. This facilitates selection. Once selected, the vectors may be isolated from the culture using routine procedures such as freeze-thaw extraction followed by purification.

Vectors containing the receptor-encoding DNA and control signals are inserted into a host cell for expression of the receptor. Some useful expression host cells include well-known eucaryotic cells. Suitable eucaryotic cells include yeast and other fungi, insect, animal cells, such as mouse L cells (a fibroblast line) COS cells and CHO cells, human cells and plant cells in tissue culture.

Depending on the host used, transformation is performed according to standard techniques appropriate to such cells. For mammalian cells the calcium phosphate precipitation method of Graeme and Van Der Eb, *Virology* 52:546 (1978) is preferred. Transformations into plants may be carried out using *Agrobacterium tumefaciens* (Shaw et al., Gene 23:315 (1983) or into yeast according to the method of Van Solingen et al. *J.Bact.* 130: 946 (1977) and Hsiao et al. *Proceedings, National Academy of Science,* 76: 3829 (1979).

Upon transformation of the selected host with an appropriate vector the polypeptide or peptide encoded can be produced, often in the form of fusion protein, by culturing the host cells. The polypeptide or peptide of the invention may be detected by rapid assays as indicated above. The polypeptide or peptide is then recovered and purified as necessary. Recovery and purification can be achieved using any of those procedures known in the art, for example by adsorption onto and elution from an anion exchange resin.

D. Ligands

Ligands that bind to receptor CMRF-35-H9 also have utility.

The ligand will usually be an antibody or an antibody binding fragment raised against receptor CMRF-35-H9 or its extracellular domain.

Such antibodies may be polyclonal but are preferably monoclonal. Monoclonal antibodies may be produced by methods known in the art. These methods include the immunological method described by Kohler and Milstein in *Nature* 256: 495–497 (1975) and Campbell in "Monoclonal Antibody Technology, the Production and Characterization of Rodent and Human Hybridomas" in Burdon et al. Eds, Laboratory Techniques in Biochemistry and Molecular Biology, Volume 13, Elsevier Science Publishers, Amsterdam (1985); as well as by the recombinant DNA method described by Huse et al. in *Science* 246: 1275–1281 (1989).

E. Ligand-Antigen Constructs

Ligands which bind to receptor CMRF-35-H9 as expressed on antigen-presenting cells (usually antibodies or antibody-binding fragments) can be coupled or otherwise associated with antigens against which an immune response is desired. In use, the ligand component binds to receptor CMRF-35-H9 and the antigen-presenting cell is 'primed' with the associated antigen. This 'priming' action will assist in the induction of an immediate immune response against the antigen.

The ligand-antigen construct can take any appropriate form for administration to the antigen-presenting cells. Such forms may differ depending upon whether the therapeutic protocol involves isolation of the patients antigen-presenting cells (so that the priming action can take place in vitro) or whether the construct is to be administered to a patient in vivo.

One example of a construct for administration to a patent in vivo is a live recombinant viral vaccine. Such a vaccine includes nucleic acid encoding the CMRF-35-H9 ligand (or a portion thereof and the antigen. The vaccine is administered to the patient and, once within the patient, expresses the encoded ligand and antigen to bind to the patients antigen-presenting cells (via receptor CMRF-35-H9).

A number of such live recombinant viral vaccine systems are known. An example of such a system is the Vaccinia virus system (U.S. Pat. No. 4,603,112; Brochier et al., *Nature* 354: 520 (1991)).

EXPERIMENTAL

Various aspects of the invention will now be described with reference to the following experiments which demonstrate that receptor CMRF-35-H9 is a molecule which is distinct from CMRF-35, and that CMRF-35-H9 binds IgM.

A. Receptor Activity of CMRF-35-H9

Materials and Methods

Antibodies: The following antibodies were used; CMRF-35 (IgG2$_a$) (Daish et al., Immunology 79:55–63 (1993)), Sal5 (agG2$_a$ isotype control, obtained from Professor H Zola, Adelaide). Flurosecein isothiocyanate-conjugated goat anti-human Fab fragments specific for human IgG, IgA and IgM chains were obtained from DAKO. The following antibodies were produced in the laboratory using standard techniques; CMRF-7 (CD15, IgM), CMRF-10 (erythrocyte b sialoglycoprotein, IgG$_1$), CMRF14 (erythrocyte a sialoglycoprotein, IgG2$_b$), CMRF-15 (erythrocyte a sialoglycoprotein, IgM), CMRF-17 (B lymphocyte activation antigen, IgM).

Immunoglobulins: Purified IgM, IgG and IgA were bought from DAKO.

Purification of IgM: Human IgM was purified from human plasma by dialysis O/N against $H_2O$ to precipitate he euglobulin. The euglobulin was dissolved in 5 mM Tris ClpHSO, 10 mM $CaCl_2$ and passed over a Sephacryl 300 column. The void eluate was run on a 4–35% gradient gel under reducing conditions to assess the purity of IgM.

Digestion of IgM: Fcm5 were prepared by digestion of IgM with trypsin at 60° C. and purified on a Sephacryl 300 column.

Aggregation of IgM and IgG: Purified IgM (10–20 mg/ml) was incubated at 63° C. for 30 minutes in glass tubes. The protein was cooled on ice and dilute with PBS pH 8.0 before pelleting the precipitate by centrifugation at 145,000 g for 60 min at RT. The pellet was resuspended in PBS pH 8.0 and used at approximately 2.5 mg/ml protein.

Cells: All cells were grown and maintained in RPMI media supplemented with 10% FCS, glutamine, penicillin and streptomycin.

Transfectants: The mouse L cell fibroblast line was transfected with an expression construct for the CMRF-35 cDNA in the pcDNA2 (Invitrogen) expression vector. Stable transfectants were selected after electroporation. Even with Geneticin selection the levels of cell surface CMRF-35 decreased over time and after preliminary experiments these transfectants were abandoned in favour of haemopoietic cell based transfectants. Jurkat cells were transfected by electroporation with the cDNAs for CMRF-35 and CMRF-35-H9 in the mammalian expression vector pcDNA3 (Invitrogen). Transfected cells were selected with 600 mg/ml Geneticin (Life Technologies) and maintained with 200 mg/ml Geneticin. Routine flow cytometry was used to monitor expression.

Flow cytometry: Cells ($0.5 \times 10^5$) were incubated on ice with saturating amounts of antibody or immunoglobulin (100 mg/ml for 30 mins, washed twice in PBS/1% BSA and then labelled with specific FITC conjugated antibody. The primary labelled cells were either analysed on the FACS Vantage or double labelled with phycoerythrin conjugated antibodies before analysis. For double labelling, the cells were washed as before and then incubated in 10% normal mouse serum for 10 mins on ice. The cells were then labelled with directly conjugated antibodies for 30 mins on ice, washed and then analysed.

Rosetting: Human A-RBC were washed in normal saline and resuspended at a 5% solution. An equal volume (25 ml) 5% RBC was incubated with (25 ml) mAb or human serum for 30 mins at 37° C. The coated cells were then washed in PBS and resuspended at 2% solution. The mAb were used at saturating concentrations and the human serum at a predetermined dilution that resulted in limited aggregation. The coated RBC were then incubated with the transfected cells for 5 mins at 37° C., pelleted at 800 rpm for 3 mins and then incubated on ice for 30 mins. The cells were stained with 1% ethyl violet and rosettes were visualised by light microscopy.

Alternatively, human serum was replaced with mouse mAb that recognised epitopes on human RBC. In particular, the following mAb were used; CMRF-7 (CD15, IgM), CMRF-10 (erythrocyte b sialoglycoprotein, IgG$_1$), CMRF14 (erythrocyte a sialoglycoprotein, IgG2$_b$), CMRF-15 (erythrocyte a sialoglycoprotein, IgM), CMRF-17 (B lymphocyte activation antigen, IgM).

Results (i) Binding of the CMRF-35 cDNA Expressed in L Cells to Mouse Ig

Expression cloning was used to isolate a cDNA that encoded the epitope for the CMRF-35 mAb. This translated sequence of this cDNA indicated that the protein had a single V-like domain indicating that it was a member of the Ig superfamily. It was most similar to the Ig binding domains (domain V1 and V4) of the Ig receptor for polymeric IgA and IgM.

To determine if the CMRF-35 cDNA expressed a molecule that bound a form of immunoglobulin, stable transfectants were made. Initially, these were made in the mouse fibroblast cell line, L cells. FIG. 3 shows that these cells expressed a cell surface molecule that bound to the CMRF-35 mAb compared to the parental L cells. Initial experiments were performed to determine if these transfectants expressed well characterised receptors for IgG. The transfectants did not bind mAb for specific CD16, CD32 or CD64 (FIG. 4). However they did appear to specifically bind mouse mAb with the IgM and IgG2$_b$ isotypes. This indicated that the CMRF-35 cell surface molecule bound the Fc portion of these two isotypes when the immunoglobulin was in a monomeric form.

(ii) Rosetting of the CMRF-35 cDNA Expressing L Cell Transfectants

Rosetting analysis was performed to determine if the binding of antibody to specific antigen resulted in conformational changes to the Fc portions of the immunoglobulin. Rosettes were formed with L cell transfectants expressing CMRF-35 and RBC coated with antibodies of the IgM isotypes but not with RBC coated with IgG2b (FIG. 6).

(iii) Expression of Both cDNAs in Haemopoietic Cells, Jurkat

Figure 1:
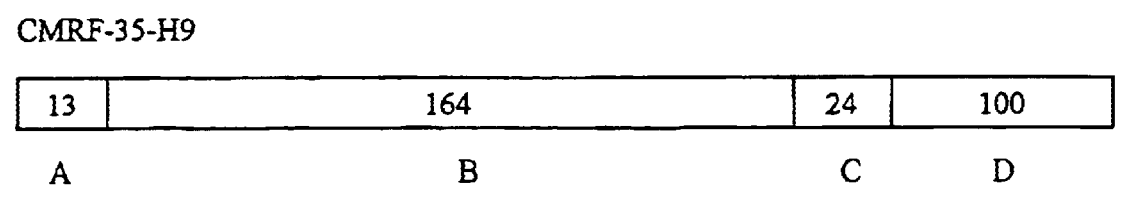

In subsequent analysis a second cDNA product was identified that encodes an epitope recognised by the CMRF-35 mAb, CMRF-35-H9 cDNA (FIG. 1). Transfectants expressing the CMRF-35 cDNA or the CMRF-35-H9 cDNA were made in the acute T lymphocyte leukaemic line, Jurkat. Stable transfectants were selected with Geneticin. Transfectants expressing either cDNA bound the CMRF-35 mAb as detected by flow cytometry (FIG. 5).

(iv) Binding of Human Immunoglobulins to the Transfectants

Monomeric IgG, IgA and IgM was incubated with the transfectants and binding effected using the second stage anti-human antibodies. FIG. 4 shows the flow cytometry profiles for the binding of the immunoglobulins to the CMRF-35-H9 expressing transfectants. CMRF-35-Ig bound mouse IgM but not mouse Ig2a or IgG 1.

Rosetting of the CMRF-35-H9 and vector only transfectants with human RBC coated with either mouse mAb or human serum were used to determine if the CMRF-35-H9 molecule was able to bind IgM. Binding of the coated RBC with the transfectants was observed.

Conclusion

Receptor CMRF-H9 binds IgM and is a distinct molecule from CMRF-35, notwithstanding that both are bound by mAb CMRF-35.

B. IgM mAb Reactivity of Cell Lines Transfected with CMRF-35-H9

Cell lines transfected with CMRF-35-H9, CMRF-35, vector only were subjected to the following procedures (untransfected cell lines being included as a control):

Cell Lysis

Cells at $10^8$/ml were solubilised by incubation (1 hr, 40° C.) of cells in lysis buffer (150 mM NaCl, 100 mM Tris, 0.02% $NaN_3$, pH7.8) containing detergent (0.5% Triton-X-100 and 0.25% CHAPS) and the protease inhibitor mix, Complete™ (Boehringer Mannheim). Following centrifugation (10,000×g, 10 min), lysates (1×$10^6$ cell equivalents/lane) were fractionated on a reducing SDS-PAGE gel and transferred to nitrocellulose (HybondC, Amersham)

Western Blot Detection

Western blot detection was performed on transfected cell lines as follows. Antigens bound to nitrocellulose membranes were renatured by overnight incubation at 37° C. in 100–200 ml PBS with gentle shaking. Membranes were blocked in 5% milk powder/PBS (1 hr, room temperature) before incubation (overnight, 4° C.) with mAb solution. For incubation with IgM isotype antibodies CMRF-75 20% human serum was added to the blocking solution. Purified mAb was used at approximately 10 μg/ml in 1% non fat milk powder (MP)/PBS solution and culture supernatant was diluted 4:1 with 5% MP/PBS and supplemented with HEPES (pH7.4) to a final concentration of 10 mM. Once again for CMRF-75 antibodies of IgM isotype 20% human serum was added to the diluent. Following incubation, membranes were washed in cold PBS (5×over 5 min) then crosslinked by incubating for 15 min with 0.25% glutaraldehyde/PBS. Membranes were then washed sequentially (15 min each wash) with; 0.1M glycine in PBS, pH8.5 (two changes used) to block residual glutaraldehyde reactive groups, 0.1% BSA/PBS, 1% MP/PBS and 0.1% goat serum (GS)/PBS. Following washing, the membranes were incubated (1 hr) with biotin conjugated goat anti-mouse Ig (Dako) diluted (1:1000) in 10% GS/PBS then washed in PBS (10 min) and briefly in 0.05% Tween 20/PBS. Membranes were then incubated (1 hr) with streptavidin conjugated horseradish peroxidase (Dako) diluted (1:1000) in 1% BSA/PBS then washed with 0.05% Tween 20/PBS. Reactive protein bands were then visualised by chemiluminesence using Super Signal (Pierce, Ill., USA) and exposure to autoradiographic film P(AR-5 Kodak). The molecular weight of visualised bands was determined by comparison with biotinylated molecular weight standards (Biorad).

The results are shown in FIG. 8. The IgM isotype antibody CMRF-75 reacted inter alia with cell lines transfected with CMRF-35-H9.

Conclusion

IgM isotype antibodies bind to cell lines expressing receptor CMRF-35-H9.

I. Utilities

The CMRF-35-H9 receptor and extracellular domain thereof have broad utilities in methods of therapy and prophylaxis. These include:

i) A method for modulating an immune response in a patient, the method comprising administering to said patient receptor CMRF-35-H9 or extracellular domain thereof or ligand or ligand-antigen construct thereto in an amount effective to modulate an immune response.

The term "modulating" is used herein to refer to stimulating, amplifying, blocking or inhibiting an immune response. The ligand will usually be an antibody or antibody binding fragment raised against receptor CMRF-35-H9 or its extracellular domains.

ii) A method for blocking or inhibiting a humoral immune response in a patient, the method comprising administering to said patient receptor CMRF-35-H9 or extracellular domain thereof in an amount effective to bind available IgM.

In one application of this method, receptor CMRF-35-H9 or the extracellular domain thereof may be administered to a patient receiving a transplant, in an amount effective to inhibit a humoral immune response in that patient.

In broad terms, the administration of the CMRF-35-H9 or extracellular domain causes antibody adsorption thereto. The adsorbed antibody is then no longer free to bind to the transplant, thereby inhibiting the humoral immune response.

The receptor domain can be administered intravenously, intramuscularly, subcutaneously, topically, orally, intranasally, rectally or intracerebroventricularly, as appropriate. Preparation of administrable forms of the receptor or domain together with pharmaceutically acceptable diluents, carriers or excipients are well known in the art.

General assistance in the preparation of such formulations may be obtained from Remingtons Pharmaceutical Sciences, 16th Edition, Easton: Mac Publishing Company (1980); The National formulary XIV 14th Edition, Washington: American Pharmaceutical Association (1975); and Goodman and Gillmans "The Pharmaceutical basis for Therapeutics", 7th Edition, the contents of which are incorporated herein by reference.

iii) A method for loading a protective antigen into an antigen presenting cell, the method comprising combing the antigen presenting cell with CMRF-35-H9 receptor/domain ligand-antigen construct. Preferably, the antigen presenting cell is a B-lymphocyte or dendritic cell, most preferably a dendritic cell.

iv) A related method for stimulating an immune response comprises loading an antigen into an antigen presenting cell according to the method of paragraph iii). Preferably the immune response is a primary T lymphocyte immune response.

v) A method for diagnosing myeloid leukaemia in a patient, comprising:
(a) determining the CMRF-35-H9 level-in a sample from said patient; and
(b) comparing the level to a known standard, an increased level of CMRF-35-H9 or decreased level of promyelocytic leukaemia being diagnostic of leukaemia.

The term "standard sample" is used to refer to a sample taken from a comparative animal or human which does not have myeloid leukaemia. A level statistically significant above the standard may be diagnostic of leukaemia.

Preferably, the sample is a blood or bone marrow sample. Most preferably, a comparison may be made of CMRF-35-H9 levels on CD34+ cells from bone marrow samples. These cells express the CMRF-35-H9 receptor indicating its utility as an early marker in the detection of myeloid leukaemia.

Those persons skilled in the art will of course appreciate that the above description is provided by way of example only and that the invention is not limited thereto.

What is claimed is:

1. Isolated receptor CMRF-35-H9 which comprises an amino acid sequence as set out in SEQ ID NO:1 which binds IgM.

2. An isolated polynucleotide which encodes receptor CMRF-35-H9 of claim 1.

3. The isolated polynucleotide of claim 2 which is DNA.

4. An Isolated polynucleotide of claim 3 which comprises the nucleotide sequence of SEQ ID NO:4.

5. Isolated receptor CMRF-35-H9 which comprises an amino acid sequence as set out in SEQ ID NO:2 which binds IgM.

6. An isolated polynucleotide which encodes a receptor CMRF-35-H9 of claim 5.

7. The polynucleotide of claim 6 which is DNA.

8. The isolated polynucleotide of claim 7 which comprises the nucleotide sequence of SEQ ID NO:5.

9. The polynucleotide of claim 7 which comprises the nucleotide sequence of SEQ ID NO:6.

10. Isolated receptor CMRF-35-H9 which comprises the extracellular domain of receptor CMRF-35-H9 and comprises an amino acid sequence of SEQ ID NO:3 which binds IgM.

11. An isolated polynucleotide which encodes a receptor CMRF-35-H9 extracellular domain of claim 10.

12. The polynucleotide of claim 11 which is DNA.

13. An isolated vector which comprises a polynucleotide sequence of claim 11.

14. A method of producing receptor CMRF-35-H9 or a peptide encoding the extracellular domain thereof comprising the steps of:

(a) culturing a suitable host cell which has been transformed or transfected with a vector as claimed in claim 13 to express the encoded receptor CMRF-35-H9 or extracellular domain; and (b) recovering the expressed product.

15. A composition comprising the receptor CMRF-35-H9 of claim 1 or 5 or 10 and one or more pharmaceutically acceptable carriers and/or diluents.

* * * * *

SEQUENCE LISTING

<160> NUMBER OF SEQ ID NOS: 6

<210> SEQ ID NO 1
<211> LENGTH: 301
<212> TYPE: PRT
<213> ORGANISM: Artificial Sequence
<220> FEATURE:
<223> OTHER INFORMATION: Description of Artificial Sequence:we really
      don't know

<400> SEQUENCE: 1

Met Trp Leu Pro Trp Ala Leu Leu Ile Trp Val Pro Gly Cys Phe
 1               5                  10                  15

Ala Leu Ser Lys Cys Arg Thr Val Ala Gly Pro Trp Gly Ser Leu Ser
                20                  25                  30

Val Gln Cys Pro Tyr Glu Lys Glu His Arg Thr Leu Asn Lys Tyr Trp
            35                  40                  45

Cys Arg Pro Pro Gln Ile Phe Leu Cys Asp Lys Ile Val Glu Thr Lys
        50                  55                  60

Gly Ser Ala Gly Lys Arg Asn Gly Arg Val Ser Ile Arg Asp Ser Pro
 65                  70                  75                  80

Ala Asn Leu Ser Phe Thr Val Thr Leu Glu Asn Leu Thr Glu Glu Asp
                85                  90                  95

Ala Gly Thr Tyr Trp Cys Gly Val Asp Thr Pro Trp Leu Arg Asp Phe
            100                 105                 110

His Asp Pro Val Val Glu Val Glu Val Ser Val Phe Pro Ala Ser Thr
        115                 120                 125

Ser Met Thr Pro Ala Ser Ile Thr Ala Ala Lys Thr Ser Thr Ile Thr
    130                 135                 140

Thr Ala Phe Pro Pro Val Ser Ser Thr Thr Leu Phe Ala Val Gly Ala
145                 150                 155                 160

Thr His Ser Ala Ser Ile Gln Glu Glu Thr Glu Val Val Asn Ser
                165                 170                 175

Gln Leu Pro Leu Leu Leu Ser Leu Leu Ala Leu Leu Leu Leu Leu
            180                 185                 190

Val Gly Ala Ser Leu Leu Ala Trp Arg Met Phe Gln Lys Trp Ile Lys
        195                 200                 205

Trp Ile Lys Ala Gly Asp His Ser Glu Leu Ser Gln Asn Pro Lys Gln
    210                 215                 220

Ala Ala Thr Gln Ser Glu Leu His Tyr Ala Asn Leu Glu Leu Leu Met
225                 230                 235                 240

Trp Pro Leu Gln Glu Lys Pro Ala Pro Arg Glu Val Glu Val Glu
                245                 250                 255

Tyr Ser Thr Val Ala Ser Pro Arg Glu Glu Leu His Tyr Ala Ser Val
            260                 265                 270

Val Phe Asp Ser Asn Thr Asn Arg Ile Ala Ala Gln Arg Pro Arg Glu
        275                 280                 285

Glu Glu Pro Asp Ser Asp Tyr Ser Val Ile Arg Lys Thr
    290                 295                 300

<210> SEQ ID NO 2
<211> LENGTH: 298
<212> TYPE: PRT
<213> ORGANISM: Artificial Sequence
<220> FEATURE:

<223> OTHER INFORMATION: Description of Artificial Sequence: we really
      don't know.

<400> SEQUENCE: 2

```
Met Trp Leu Pro Trp Ala Leu Leu Ile Trp Val Pro Gly Cys Phe
 1               5                  10                  15

Ala Leu Ser Lys Cys Arg Thr Val Ala Gly Pro Trp Gly Ser Leu Ser
            20                  25                  30

Val Gln Cys Pro Tyr Glu Lys Glu His Arg Thr Leu Asn Lys Tyr Trp
        35                  40                  45

Cys Arg Pro Pro Gln Ile Phe Leu Cys Asp Lys Ile Val Glu Thr Lys
    50                  55                  60

Gly Ser Ala Gly Lys Arg Asn Gly Arg Val Ser Ile Arg Asp Ser Pro
65                  70                  75                  80

Ala Asn Leu Ser Phe Thr Val Thr Leu Glu Asn Leu Thr Glu Glu Asp
                85                  90                  95

Ala Gly Thr Tyr Trp Cys Gly Val Asp Thr Pro Trp Leu Arg Asp Phe
            100                 105                 110

His Asp Pro Val Val Glu Val Glu Val Ser Val Phe Pro Ala Ser Thr
        115                 120                 125

Ser Met Thr Pro Ala Ser Ile Thr Ala Ala Lys Thr Ser Thr Ile Thr
    130                 135                 140

Thr Ala Phe Pro Pro Val Ser Ser Thr Thr Leu Phe Ala Val Gly Ala
145                 150                 155                 160

Thr His Ser Ala Ser Ile Gln Glu Glu Thr Glu Val Val Asn Ser
                165                 170                 175

Gln Leu Pro Leu Leu Leu Ser Leu Leu Ala Leu Leu Leu Leu Leu Leu
                180                 185                 190

Val Gly Ala Ser Leu Leu Ala Trp Arg Met Phe Gln Lys Trp Ile Lys
            195                 200                 205

Ala Gly Asp His Ser Glu Leu Ser Gln Asn Pro Lys Gln Ala Ala Thr
            210                 215                 220

Gln Ser Glu Leu His Tyr Ala Asn Leu Glu Leu Met Trp Pro Leu
225                 230                 235                 240

Gln Glu Lys Pro Ala Pro Pro Arg Glu Val Glu Val Glu Tyr Ser Thr
                245                 250                 255

Val Ala Ser Pro Arg Glu Glu Leu His Tyr Ala Ser Val Val Phe Asp
            260                 265                 270

Ser Asn Thr Asn Arg Ile Ala Ala Gln Arg Pro Arg Glu Glu Pro
            275                 280                 285

Asp Ser Asp Tyr Ser Val Ile Arg Lys Thr
    290                 295
```

<210> SEQ ID NO 3
<211> LENGTH: 164
<212> TYPE: PRT
<213> ORGANISM: Artificial Sequence
<220> FEATURE:
<223> OTHER INFORMATION: Description of Artificial Sequence: we really
      don't know.

<400> SEQUENCE: 3

```
Gly Cys Phe Ala Leu Ser Lys Cys Arg Thr Val Ala Gly Pro Trp Gly
 1               5                  10                  15

Ser Leu Ser Val Gln Cys Pro Tyr Glu Lys Glu His Arg Thr Leu Asn
            20                  25                  30
```

```
Lys Tyr Trp Cys Arg Pro Pro Gln Ile Phe Leu Cys Asp Lys Ile Val
            35                  40                  45

Glu Thr Lys Gly Ser Ala Gly Lys Arg Asn Gly Arg Val Ser Ile Arg
 50                  55                  60

Asp Ser Pro Ala Asn Leu Ser Phe Thr Val Thr Leu Glu Asn Leu Thr
 65                  70                  75                  80

Glu Glu Asp Ala Gly Thr Tyr Trp Cys Gly Val Asp Thr Pro Trp Leu
                 85                  90                  95

Arg Asp Phe His Asp Pro Val Val Glu Val Glu Val Ser Val Phe Pro
                100                 105                 110

Ala Ser Thr Ser Met Thr Pro Ala Ser Ile Thr Ala Ala Lys Thr Ser
            115                 120                 125

Thr Ile Thr Thr Ala Phe Pro Pro Val Ser Ser Thr Thr Leu Phe Ala
            130                 135                 140

Val Gly Ala Thr His Ser Ala Ser Ile Gln Glu Thr Glu Glu Val
145                 150                 155                 160

Val Asn Ser Gln

<210> SEQ ID NO 4
<211> LENGTH: 903
<212> TYPE: DNA
<213> ORGANISM: Artificial Sequence
<220> FEATURE:
<223> OTHER INFORMATION: Description of Artificial Sequence: we really
      don't know.

<400> SEQUENCE: 4
atgtggctgc cttgggctct gttgcttctc tgggtcccag gatgttttgc tctgagcaaa      60
tgcaggaccg tggcgggccc gtggggatcc ctgagtgtgc agtgtcccta tgagaaggaa     120
cacaggaccc tcaacaaata ctggtgcaga ccaccacaga ttttcctatg tgacaagatt     180
gtggagacca aagggtcagc aggaaaaagg aacggccgag tgtccatcag ggacagtcct     240
gcaaacctca gcttcacagt gaccctggag aatctcacag aggaggatgc aggcacctac     300
tggtgtgggg tggatacacc atggctccga gactttcatg atcccgttgt cgaggttgag     360
gtgtccgtgt tcccggcatc aacgtcaatg acacctgcaa gtatcactgc ggccaagacc     420
tcaacaatca caactgcatt tccacctgta tcatccacta ccctgtttgc agtgggtgcc     480
acccacagtg ccagcatcca ggaggaaact gaggaggtgg tgaactcaca gctcccgctg     540
ctcctctccc tgctggcatt gttgctgctt ctgttggtgg gggcctccct gctagcctgg     600
aggatgtttc agaaatggat caatggatc aaagctggtg accattcaga gctgtcccag     660
aaccccaagc aggctgccac gcagagtgag ctgcactacg caaatctgga gctgctgatg     720
tggcctctgc aggaaaagcc agcaccacca agggaggtgg aggtggaata cagcactgtg     780 gcctcccca gggaagaact tcactatgcc tcggtggtgt ttgattctaa caccaacagg     840
atagctgctc agaggcctcg ggaggaggaa ccagattcag attacagtgt gataaggaag     900
aca                                                                   903

<210> SEQ ID NO 5
<211> LENGTH: 894
<212> TYPE: DNA
<213> ORGANISM: Artificial Sequence
<220> FEATURE:
<223> OTHER INFORMATION: Description of Artificial Sequence: we really
      don't know.

<400> SEQUENCE: 5
```

```
atgtggctgc cttgggctct gttgcttctc tgggtcccag gatgtttttgc tctgagcaaa      60 tgcaggaccg tggcgggccc gtggggatcc ctgagtgtgc agtgtcccta tgagaaggaa     120
cacaggaccc tcaacaaata ctggtgcaga ccaccacaga ttttcctatg tgacaagatt     180
gtggagacca aagggtcagc aggaaaaagg aacggccgag tgtccatcag ggacagtcct     240
gcaaacctca gcttcacagt gaccctggag aatctcacag aggaggatgc aggcacctac     300
tggtgtgggg tggatacacc atggctccga gactttcatg atcccgttgt cgaggttgag     360
gtgtccgtgt tcccggcatc aacgtcaatg acacctgcaa gtatcactgc ggccaagacc     420
tcaacaatca aactgcatt tccacctgta tcatccacta ccctgtttgc agtgggtgcc      480
acccacagtg ccagcatcca ggaggaaact gaggaggtgg tgaactcaca gctcccgctg     540
ctcctctccc tgctggcatt gttgctgctt ctgttggtgg gggcctccct gctagcctgg     600
aggatgtttc agaaatggat caaagctggt gaccattcag agctgtccca gaaccccaag     660
caggctgcca cgcagagtga gctgcactac gcaaatctgg agctgctgat gtggcctctg     720
caggaaaagc cagcaccacc aagggaggtg gaggtggaat acagcactgt ggcctccccc     780
agggaagaac ttcactatgc ctcggtggtg tttgattcta acaccaacag gatagctgct     840
cagaggcctc gggaggagga accagattca gattacagtg tgataaggaa gaca           894
```

<210> SEQ ID NO 6
<211> LENGTH: 492
<212> TYPE: DNA
<213> ORGANISM: Artificial Sequence
<220> FEATURE:
<223> OTHER INFORMATION: Description of Artificial Sequence: we really
    don't know.

<400> SEQUENCE: 6

```
ggatgttttg ctctgagcaa atgcaggacc gtggcgggcc cgtggggatc cctgagtgtg      60
cagtgtccct atgagaagga acacaggacc ctcaacaaat actggtgcag accaccacag     120
attttcctat gtgacaagat tgtggagacc aaagggtcag caggaaaaag gaacggccga     180
gtgtccatca gggacagtcc tgcaaacctc agcttcacag tgaccctgga gaatctcaca     240
gaggaggatg caggcaccta ctggtgtggg gtggatacac catggctccg agactttcat     300
gatcccgttg tcgaggttga ggtgtccgtg ttcccggcat caacgtcaat gacacctgca     360
agtatcactg cggccaagac ctcaacaatc aaactgcatt tccacctgt atcatccact      420 accctgtttg cagtgggtgc cacccacagt gccagcatcc aggaggaaac tgaggaggtg     480
gtgaactcac ag                                                         492
```